United States Patent [19]

Chatenever et al.

[11] Patent Number: 4,781,448
[45] Date of Patent: Nov. 1, 1988

[54] ZOOM LENS ADAPTER FOR ENDOSCOPIC CAMERA

[75] Inventors: David Chatenever; Stephen M. Kurtzer, both of Santa Barbara, Calif.

[73] Assignee: Medical Concepts Inc., Santa Barbara, Calif.

[21] Appl. No.: 20,775

[22] Filed: Mar. 2, 1987

[51] Int. Cl.⁴ .......................... G02B 7/10; G02B 23/26
[52] U.S. Cl. .................................. 350/429; 350/96.26
[58] Field of Search ...................... 350/429, 430, 96.26

[56] References Cited

U.S. PATENT DOCUMENTS

| | | | |
|---|---|---|---|
| 3,090,282 | 5/1963 | Angenieux | 350/429 |
| 3,981,564 | 9/1976 | Hoos | 350/429 |
| 4,281,907 | 8/1981 | Kamata | 350/429 |
| 4,380,378 | 4/1983 | Tamura | 350/429 |
| 4,500,181 | 2/1985 | Takahashi | 350/96.26 |
| 4,558,691 | 12/1985 | Okada | 350/96.26 |
| 4,611,888 | 9/1986 | Prenovitz et al. | 350/96.26 |

Primary Examiner—John K. Corbin
Assistant Examiner—Loha Ben
Attorney, Agent, or Firm—Elliott N. Kramsky

[57] ABSTRACT

An adapter for coupling an endoscope to a camera head. The adapter includes a zoom ring, barrel, focusing ring and chassis. A lens, slidably mounted within the barrel, moves axially within the barrel in response to rotation of the zoom ring thereby varying the transmitted size of the image of the proximal end of the endoscope. Rotation of the focusing ring produces axial movement of the barrel within the chassis for focusing the image at the camera head.

10 Claims, 3 Drawing Sheets

ZOOM LENS ADAPTER FOR ENDOSCOPIC CAMERA

BACKGROUND

1. Field of the Invention

The present invention relates to apparatus for use with endoscopic medical video equipment. More particularly, this invention pertains to an endoscopic adapter including a zoom lens.

2. Description of the Prior Art

The advent of various endoscopic instruments has proven to be a significant aid to diagnosis and to surgical procedures. Such instruments generally include an elongated probe for penetration and viewing of otherwise inaccessible body regions. The physician is able to view the body region adjacent to the distal end of the probe through an eyepiece near the proximal end. Examples of endoscopic instruments include the laparoscope, cystoscope, arthroscope, bronchoscope, colonoscope, etc. the functions and areas of use of which are apparent from the nomenclature.

While providing a substantial technical advance, the utility of the endoscope has been significantly increased by the development of video cameras for coupling to the image output of the endoscope. The use of such a camera protects the vision of the physician in those instances in which a highly-reflective medium must be viewed with bright illumination. This often occurs in arthoscopic surgery where high intensity illumination of reflective articular tissue can cause injury to the retina of an operating physician.

The combination of video camera with the endoscope, as opposed to direct viewing, promotes the operator comfort and, hence, instrument utility. When using a camera, the physician needn't position himself throughout the examination to accommodate an eyepiece located near the proximal end of the endoscope. An assistant may hold and position the endoscope while the operating physician's hands are freed to manipulate the surgical tools. As the physician and his assistant may view the image at the same time on a common monitor, prompt and accurate movement of the scope is assured throughout the operation. Thus tissue trauma due to movements of the scope is lessened.

Finally, the incorporation of a video camera permits both recordation and real time transmission of procedures. This opens many possibilities not offered by conventional endoscopy including real time consultations (and teaching) from distant venues and significant documentation benefits.

The adaptation of video camera technology to endoscopic imaging requires a means for adapting the conventional endoscope to a video camera head. Conventional apparatus for this purpose includes a mechanism for grasping the endoscope that is, in turn, coupled at its opposed end to the camera head. (Fixed focal length optics, within the adapter, transmit a circular image of the proximal end of the endoscope to the camera head for viewing on a monitor.) Means are provided in association with the adapter for focusing the image.

The size of the image of the proximal end of an endoscope is a function of probe diameter. Probes may vary in diameter from less than two (2) millimeters to approximately twelve (12) millimeters. For example, arthroscopic joint surgery generally requires an approximately four (4) millimeter diameter probe while twelve (12) millimeter probes are utilized for laparoscopy (abdominal cavity surgery).

Viewing clarity is, of course, essential to the physician. Generally the image should occupy approximately eighty (80) per cent of the height of the screen of a standard monitor to provide sufficient detail. Unfortunately, the fixed focal length optics of the conventional adapter cannot adjust image size to compensate for the different endoscopic procedures (and correspondingly different sized probes) the physician may desire to perform.

Diagnosing and operating physicians work most advantageously with little variation of image sizes. As a result, the physician has been required to maintain a number of adapters of different fixed focal lengths to compensate the image sizes produced by the probes utilized in different procedures. Such adapters are relatively expensive optical instruments. A "complete" set (by today's standards) covers a range of 25 to 40 millimeters (3 to 4 millimeter increments). Due to the expense, a physician typically purchases three adapters (25, 32 and 38 millimeter focal lengths). This represents a rough compromise between cost and viewing convenience.

Since an endoscope is employed within a critical environment, the entire system must be disinfected before use. Prior to use the components are generally immersed in a disinfecting bath for about fifteen minutes, then dried and assembled for use. The presence of even minute residual amounts of condensation on the front lens of the adapter can significantly effect viewing clarity.

Some procedures may require a change in magnification during use to permit closer viewing of the critical site. Such a substitution, of course, multiplies the chance that the physician's view will be hampered by condensation induced problems. Resulting delays can significantly hinder both diagnoses and surgical procedures.

SUMMARY

The foregoing and other shortcomings of the prior art are addressed and overcome by the present invention that provides an adapter for coupling an image from an endoscope. The adapter includes a substantially cylindrical barrel for retaining a coaxial optical system that comprises a plurality of lenses. Means are provided for continuously varying the focal length of the adapter.

The foregoing features and advantages of the invention will become further apparent from the detailed description that follows. Such description is accompanied by a set of illustrative drawing figures. The drawing figures and the written description include numerals that point to the various features of this invention, like numerals referring to like features throughout both the written description and the drawings.

DETAILED DESCRIPTION

Figure 1:
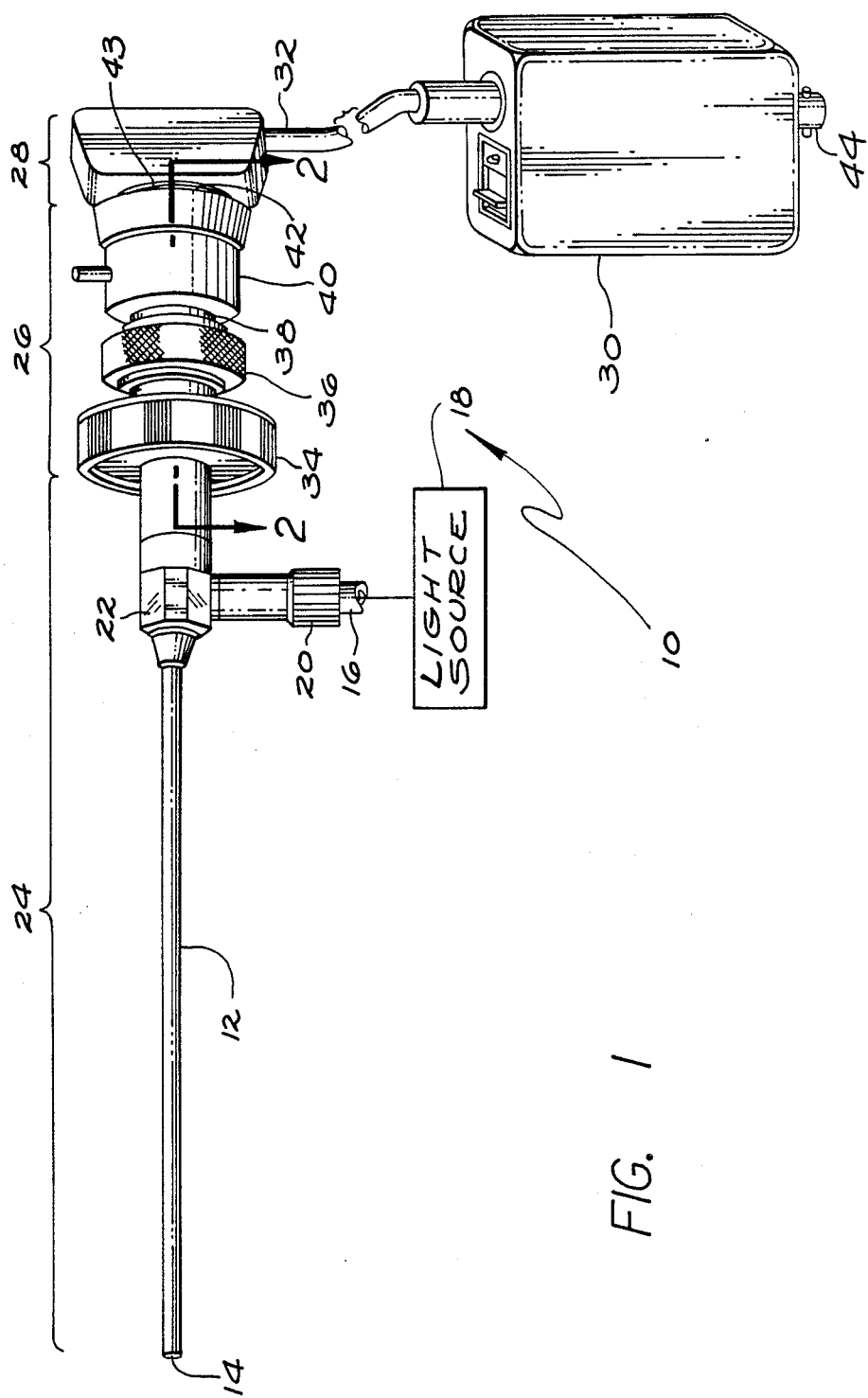
FIG. 1 is a perspective view of an endoscope including an optical system in accordance with the invention.

Turning now to the drawings, FIG. 1 is a perspective view of a medical diagnostic apparatus 10 that includes an improved optical system in accordance with the invention. The apparatus 10 generally comprises a probe 12 for insertion into either an anatomical cavity or an incision. A window 14 that admits an illuminated view of the adjacent anatomy for transmitting to the opposed or proximal end of the probe 12 (without noticeable degradation) is provided at the probe's distal end. As will be seen, the invention is substantially directed to overcoming the problems that arise from the substantial variation in the sizes of the internal optics associated with different types of endoscopes.

Illumination enters the probe 12 through a light guide 16 that accepts the output of a light source 18. A tightening ring 20 is provided at the end of the guide 16 to permit the transmitted light to be coupled into the probe 12 through the body 22 of the endoscope 24.

The probe 12 is the only portion of the system 10 that actually enters the body. It may be of either rigid stainless steel or flexible optical fiber construction and may possess various dimensions in accordance with its intended use. For example, rigid constructions may range from six (6) inches to a couple of feet in length and from less than two (2) to twelve (12) millimeters in diameter. Upper and lower gastrointestinal ("G.I.") procedures require flexible probes. Bronchoscopes are generally at the lower end of the diameter scale while upper G.I. scopes for esophageal and stomach procedures fall into the ten-to-twelve millimeter range. Twelve millimeter diameter colonoscopes of about one and one-half meters in length are used for lower G.I. procedures.

In one application of the endoscope (i.e. without video camera) an eyecup and ocular lens arrangement is located at the end opposite the probe end of the body 22. However, in a standard medical video arrangement, the lens system is associated with an adapter 26 for coupling the image output of the endoscope 24 into a video camera head 28 that is, in turn, electrically connected to a camera processor 30 by means of a conductor 32.

A compact and watertight adapter 26 in accordance with this invention includes a grasping mechanism 34, zoom ring 36, barrel 38, focusing ring 40 and chassis 42. The grasping mechanism 34 comprises conventional apparatus, such as a plurality of projecting tines, for removably engaging the adapter 26 to the eye cup of the endoscope 24. A zoom lens, mounted within the barrel 38, is axially movable within the barrel 38 relative to a group of lenses fixed therein in response to rotation of the zoom ring 36, to vary the size of the image transmitted through the adapter 26 and achieve zooming. By incorporating an optical system that includes a zoom capability, the adapter of the invention enables the physician to maintain appropriate magnification regardless of the size of the probe employed. As a result, the costly and unwieldy set of adapters commonly utilized by the physician is unnecessary. A single adapter unit is provided that accommodates all image sizes. As the focusing ring 40 is rotated, the barrel 38 and the lenses mounted therein move as a group axially within the chassis 42 and relative to the camera head 28 to produce a focused image at the camera head 28, whereby focusing of the adapter is achieved. With the exception of lenses and o-rings discussed infra, the adapter 26 is of metallic construction preferably comprising aluminum that has been anodized for appropriate hardness.

The focussed image that emerges from the adapter 26 is detected by a pickup device, such as a CCD sensor, of the camera head 28. The camera head 28 additionally includes preamplifier, line driving and receiving circuitry for communicating with the camera processor 30. The pixels of the CCD sensor are read out decoded, processed and encoded into standard video display formats. An output port 44 is provided for inserting either video monitor(s) or recording apparatus.

As shown in FIG. 1, the camera head 28 is separate from the adapter 26, including a conventional "C" mount 43. The end of the adapter 26 is accordingly arranged to interlock readily with the camera head 28. However, the teachings of this invention are equally applicable to an endoscopic system wherein the adapter and camera head form an integral unit.

Figure 2:
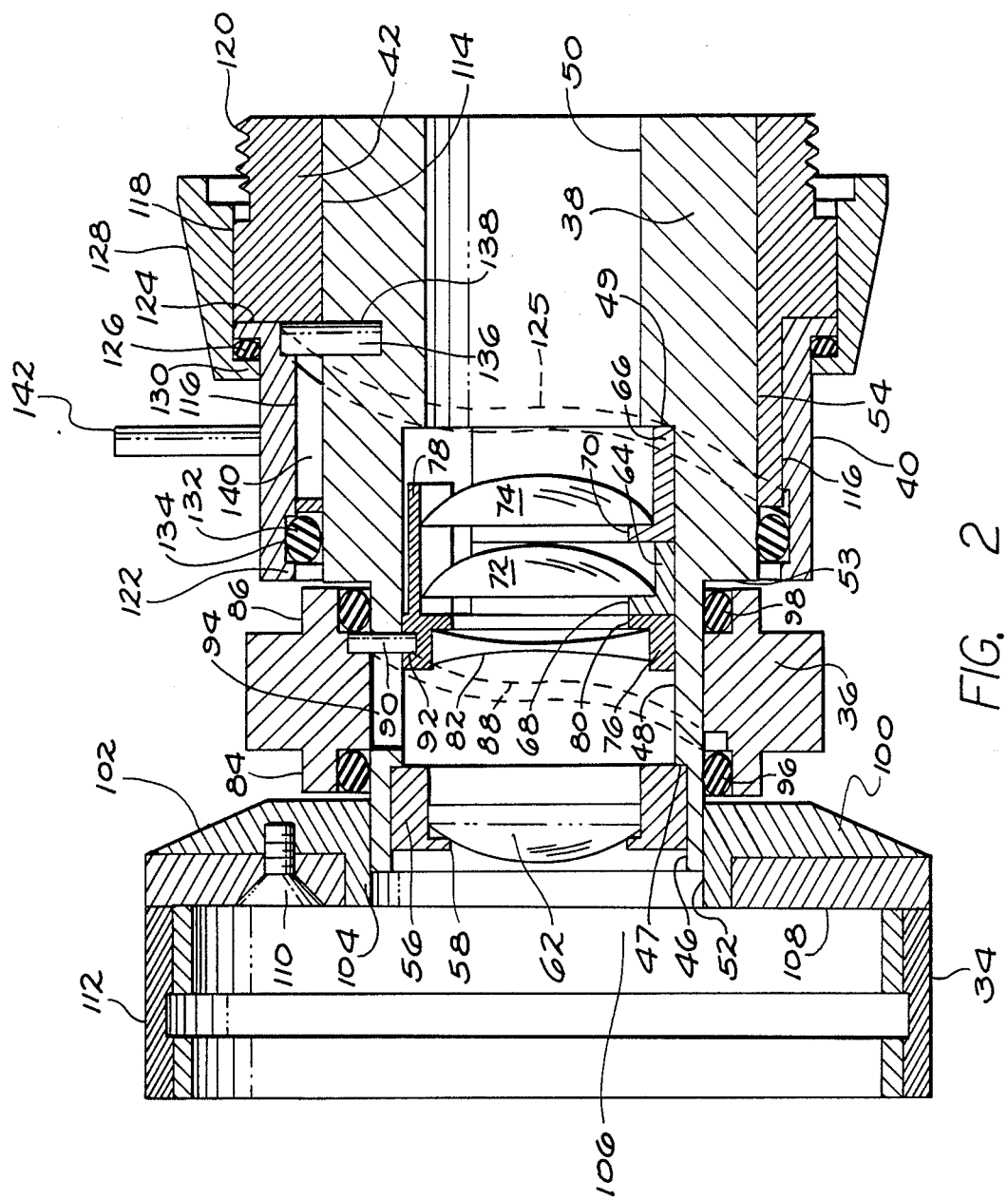
FIG. 2 is an enlarged side sectional view of the endoscope adapter, taken along section line 2—2 of FIG. 1.

FIG. 2 is an enlarged partial side sectional view of the endoscope adapter 26, taken along the section line 2—2 of FIG. 1. The generally cylindrically shaped barrel 38 houses the zoom and focusing optics. The barrel 38, preferably machined from a single piece of metal, comprises interior sections 46, 48 and 50 of differing diameters thereby forming shoulders 47 and 49 as shown. The exterior of the barrel 38 includes a reduced diameter front section 52 and rear section 54 forming shoulder 53 therebetween.

A circular collar 56 has an inwardly directed flange 58. The outside diameter of the collar 56 is identical to the inside diameter of the barrel section 46 within which it is positioned so as to abut the shoulder 47. The collar 56 is sealably secured in place by conventional watertight gluing means to prevent commonly utilized sterilizing solutions from entering the barrel 38. The flange 58 acts as a stop for a convergent plano-convex circular lens 62 of optical quality glass that is press-fit interior of the collar 56 and secured by the waterproof optical cement.

A pair of "C" shaped collars 64 and 66 of different lengths include circular interior flanges 68, 70. The collars 64, 66 are fitted within the dimensionally-matching section 48 of the barrel 38. One edge of the collar 66 is sealably secured against the shoulder 49. Abutting the opposed edge of the collar 66 and secured thereto is the collar 64. Pressed interior to collars 64, 66 and secured to the flanges 68, 70 as shown by waterproof optical cement are plano-convex circular lenses 72, 74. Thus, it may be seen that the plano-convex lenses 62, 72 and 74 comprise a group of lenses fixed within the barrel 38 for axial movement with it.

A fourth collar 76 mounted within the barrel section 48 includes a semi-cylindrical tongue 78 that extends into an opening formed between the collars 64, 66. (The relationship between the collars 64, 66 and the tongue 78 of the collar 76 will become further apparent in FIG. 3.) The collar 76 is moveable axially within the barrel 38 and has an interiorly-directed flange 80 to which a circular biconcave zoom lens 82 is fixed by optical cement. The curvature, thickness and separation distances relating to the coaxially aligned arrangement of lenses 62, 82, 72 and 74 are determined in accordance with the variable focal length (typically twenty five (25) to fifty (50) millimeters) optical prescription of the adapter. The mechanisms of the adapter enables the user to achieve this highly-desirable optical range without violating the inherent size constraints imposed by the operating/diagnostic environment.

The annular zoom ring 36 encircles the barrel 38. The ring 36 includes an opposed pair of circular flanges 84 and 86. A helical slot 88 is formed in the interior surface of the ring 36. A pin 90 is press-fit into a circular hole 92 that is formed in the exterior surface of the collar 76 and extends through an elongated slot 94 in the barrel 38 so that its bottom portion rests within the helical slot 88. As the zoom ring 36 is rotated about the circumference of the barrel 38, the collar 76 is thereby driven in an axial direction within and relative to the section 48 of the barrel 38 by the action of the pin 90 as it follows the helical slot or groove 88. The resultant axial movement of the biconcave zooming lens 82 within the barrel 38 and relative to "fixed" lenses 62, 72 and 74 adjusts the focal length, and resultant magnification, of the optical system comprising lenses 62, 82, 72 and 74, thereby zooming the adapter. A pair of elastomeric o-rings 96 and 98 are located between the barrel 38 and the ring flanges 84 and 86 respectively. The o-rings 96, 98 seal the interior of the barrel 38 to prevent fluids from entering through the slot 94 while permitting the required rotational movement of the ring 36 with respect to the barrel 38.

A circular front plate 100 has an internal bore of the same diameter as the exterior surface of barrel section 46. The plate 100 is press-fit onto the barrel 38 adjacent the zoom ring 36. The inclined rear exterior surface 102 of the plate 100 facilitates the user's access for rotation of the ring 36.

The somewhat cup-shaped grasping mechanism 34 has a circular central aperture 106 in the rear wall 108 thereof. The mechanism 34 is so located that the aperture 106 fits over an axial flange 104 of the plate 100. The mechanism 34 is secured to the front plate 100 by conventional means, such as stainless steel screws 110 separated by one-hundred twenty (120) degrees about the rear wall 108 or the like. As mentioned previously, the mechanism 34 may include a retractable tines assembly responsive to rotation of a ring 112 for removably securing the endoscope 24 to the adapter 26.

The generally cylindrical chassis 42 has an internal bore 114 and external surface sections 116 and 118 of differing diameters, the rear section 118 being greater. The rear surface section 118 includes a threaded surface region 120 for engaging the "C" mount of the camera head, discussed above. Mounted within the bore 114 with matching external diameter is section 54 of the barrel 38. As will become apparent, the focus ring 40 serves to retain the barrel 38 within the bore 114.

The cylindrical focus ring 40 has inwardly and outwardly directed flanges 122 and 124 at its opposed ends. The interior surface of the ring 40 includes both a radial groove 134 and a helical slot 125. The rear portion of the ring 40 overlies section 116 of the chassis 42 so that the flange 124 abuts the shoulder that lies between the chassis sections 116 and 118. A sealing o-ring 126 encircles the focus ring 40 and abuts the opposed surface of flange 124. The o-ring 126 is captured by means of an annular collar 128 that includes an interiorly directed edge flange 130. The collar 128 is press-fit onto chassis section 118 so that the flange 130 exerts a retaining inward force against the o-ring 126. An o-ring 132 is similarly captured within the groove 134 of focus ring 40 to thereby encircle the barrel 38. The o-rings 126, 132 in combination thus seal the interior of the optical arrangement against the intrusion of undesired liquids during the disinfection process while permitting the necessary relative rotational and axial movement of the ring 40 with respect to the barrel 38.

A pin 136 is press-fit into an aperture 138 in the surface of the barrel 38. The pin 136 extends through an elongated slot 140 of the chassis 42 to engage, and be captured within, the helical slot 125. As the focus ring 40 is rotated by use of a protruding baton 142, the barrel 38 is guided axially within chassis 42 by the movement of the pin 136 within the helical slot 125. As a consequence the axial position of the optical system is adjusted with respect to the camera head 28. Such relative movement permits the user to focus the image transmitted through the adapter 26 in much the same way that rotation of the ring 36, producing movement of the lens 82 relative to lens 62, 72 and 74, produces the optical magnification or zoom effect discussed above.

Figure 3:
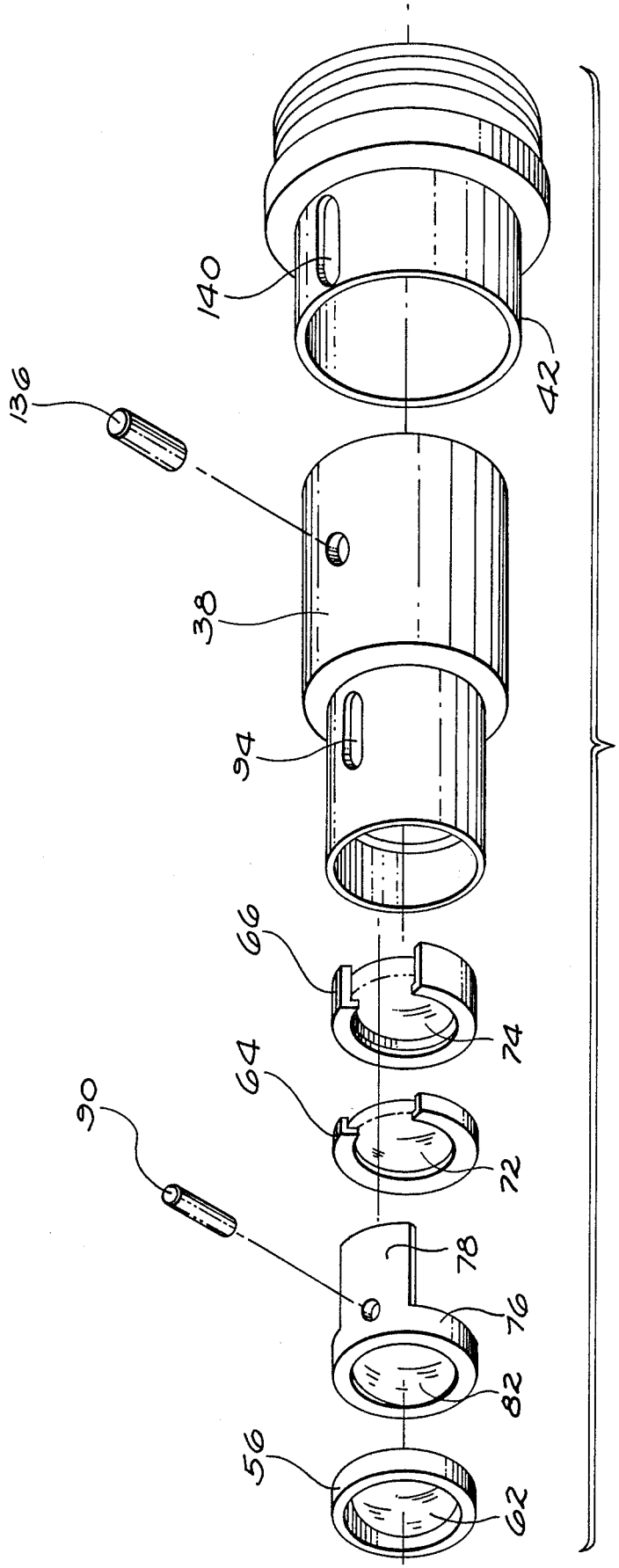
FIG. 3 is an exploded perspective view of selected elements of the adapter and related structure for clarifying the assembly and operation thereof.

FIG. 3 is an exploded perspective view of a number of the elements of the adapter assembly chosen for the purpose of clarifying the interactions that permit the adapter to function as both a focus and zoom optical element. As is seen, the lenses 62, 82, 72 and 74 which comprise the adapter optics are retained by the collars 56, 76, 64 and 66 respectively. The adapter of the invention provides a means that permits the user to manipulate the lens/optical system sequentially to achieve seperate but continuous adjustment of both magnification and focus and thus removes the necessity for multiple adapters that exists in the prior art apparatus.

The adapter, which includes a barrel 38 that is located within, and coaxial with, a chassis 42 is arranged whereby the user may sequentially adjust both magnification and focus by rotation of external rings engaging to pins 90 and 136 respectively. Elongated slots 94 and 140 in the barrel 38 and the chassis 42 permit longitudinal travel of the pins within internal helical grooves of the external rings.

By providing apparatus as above-described one may attain significant optical advantages in a watertight assembly. Lenses are chosen so that the adapter is sufficiently small (about 1.5 inches in length) to permit the physician to perform necessary movement during diagnoses and/or operation. Size constraints limit the length of the optical assembly to about one-half inch and constrain lens travel for zoom operation to about 5 millimeters.

Thus it is seen that an improved endoscopic adapter has been brought to the medical arts. By employing an adapter that utilizes the principles and structures taught herein, the advantages offered by the coupling of endoscopic instruments with medical video equipment are maximized as image size on the viewing monitor is maintained constant during substitution of various-sized endoscope probes.

While this invention has been described with reference to its presently preferred embodiment, its scope is not limited thereto. Rather, such scope is limited only insofar as defined by the following set of claims and includes all equivalents thereof.

What is claimed is:

1. An adapter, including a zoom lens, for coupling an image from the output of an endoscope to the input of a camera, comprising:
   a cylindrical barrel having first and second ends;
   coupling means for coupling said first end of said barrel coaxially to said output of said endoscope;
   mounting means for mounting said second end of said barrel coaxially to said input of said camera for axial movement relative thereto;

a sealed optical system comprising a plurality of lenses mounted coaxially within said barrel for receiving an image from said endoscope and transmitting said image through said input of said camera to an image plane therein, at least one of said lenses being axially moveable within said barrel and relative to others of said lenses for adjusting the magnification of said image on said plane, said barrel and said lenses being moveable together axially relative to said camera for focusing said image on said plane;

adjusting means for moving said one lens axially within said barrel and relative to said others; and focusing means, operatively independent of said adjusting means, for moving said barrel and said lenses axially relative to said camera.

2. The adapter of claim 1, wherein said adjusting means further comprise:

an annular zoom ring rotatably supported coaxially on said barrel, said ring having an internal circumferential surface with a helical groove formed therein;

a pin having a first end fixed on said at least one lens and a second end engaged in said groove and responsive to rotation of said ring to move said at least one lens axially within said barrel and relative to said others; and means for preventing rotation of said at least one lens during said axial movement thereof.

3. The adapter of claim 2, wherein said means for preventing rotation of said at least one lens further comprise:

said barrel containing an elongated axial slot with said pin extending radially therethrough.

4. The adapter of claim 2, wherein said zoom ring further contains a pair of coaxial counterbores in opposite ends thereof, and wherein said adapter is dynamically sealed at said zoom ring by a pair of resilient o-rings disposed, one in each of said counterbores, in radial compression between said barrel and said ring.

5. The adapter of claim 1, wherein said mounting means further comprise:

a cylindrical chassis having means at one end for mounting said chassis to said input of said camera and a coaxial bore extending therethrough; and means for slidably retaining said second end of said barrel coaxially within said bore.

6. The adapter of claim 5, wherein said focusing means further comprise:

an annular focusing ring rotatably supported coaxially on said chassis, said focusing ring having an internal circumferential surface with a helical groove formed therein;

a pin having a first end fixed in said barrel and a second end engaged in said groove and responsive to rotation of said focusing ring to move said barrel axially within said chassis and relative to said camera; and means for preventing rotation of said barrel during said axial movement thereof.

7. The adapter of claim 6, wherein said means for preventing rotation of said barrel further comprise:

said chassis containing an elongated axial slot with said pin extending radially therethrough.

8. The adapter of claim 6, wherein said focusing ring further includes an annular groove formed in said internal circumferential surface at an end disposed away from said camera, and an outer radial flange at an end disposed toward said camera, and further comprising:

an annular collar fitted coaxially on said chassis, said collar having an inward radial flange at an end disposed away from said camera and axially overlapping said outer flange on said focusing ring to retain said ring on said chassis against axial movement, said flanges defining an annular recess therebetween; and a pair of resilient o-rings, one disposed in said annular groove in radial compression between said barrel and said ring, and the other disposed in said annular recess in axial compression between said flanges, for dynamically sealing said adapter at said focusing ring.

9. The adapter of claim 1, wherein said optical system further comprises:

a first plano-convex lens fixed coaxially in said first end of said barrel;

a pair of plano-convex lenses fixed coaxially in said barrel and spaced apart from said first lens; and a double-concave lens disposed coaxially in said barrel between said first lens and said pair for axial movement therebetween.

10. The adapter of claim 1, wherein said optical system has a continuously adjustable focal length of from about 25 to about 40 millimeters.

* * * * *